United States Patent
Fuda et al.

(10) Patent No.: US 7,135,430 B2
(45) Date of Patent: Nov. 14, 2006

(54) METHOD OF TREATING FLUORINE COMPOUNDS AND TREATED SUBSTANCE

(75) Inventors: Kiyoshi Fuda, Akita (JP); Toshiaki Matsunaga, Akita (JP); Takeshi Kamiya, Akita (JP); Kota Omori, Akita (JP)

(73) Assignee: JEMCO Inc., Akita (JP)

( * ) Notice: Subject to any disclaimer, the term of this patent is extended or adjusted under 35 U.S.C. 154(b) by 406 days.

(21) Appl. No.: 10/809,354

(22) Filed: Mar. 26, 2004

(65) Prior Publication Data

US 2005/0004410 A1 Jan. 6, 2005

Related U.S. Application Data

(62) Division of application No. 10/088,073, filed as application No. PCT/JP01/06452 on Jul. 26, 2001, now Pat. No. 6,897,344.

(30) Foreign Application Priority Data

Jul. 27, 2000 (JP) ............................. 2000-227191
Jul. 6, 2001 (JP) ............................. 2001-206241

(51) Int. Cl.
*B01J 20/02* (2006.01)
*B01J 20/04* (2006.01)
*B01J 20/06* (2006.01)
*B01J 20/08* (2006.01)

(52) U.S. Cl. ....................... 502/414; 502/400; 502/401; 502/406; 502/411

(58) Field of Classification Search ................ 502/400, 502/401, 406, 411, 414
See application file for complete search history.

(56) References Cited

U.S. PATENT DOCUMENTS 4,282,162 A 8/1981 Kuhls
6,743,957 B1 6/2004 Fuda et al.

FOREIGN PATENT DOCUMENTS

| | | |
|---|---|---|
| JP | 6-48742 | 2/1994 |
| JP | 10-279307 | 10/1998 |
| WO | 94/10973 | 5/1994 |

OTHER PUBLICATIONS

76th Spring Meeting of Chemical Society of Japan, Mar. 1999 (with English Abstract).

*Primary Examiner*—Elvis O. Price
(74) *Attorney, Agent, or Firm*—Oblon, Spivak, McClelland, Maier & Neustadt, P.C.

(57) ABSTRACT

Divalent and trivalent metal salts are added to the solution containing the fluorine compound to precipitate the layered double hydroxide containing the fluorine compound between layers. By these processes, the fluorine compound can be fixed with high rate. Moreover, if necessary, the precipitated layered double hydroxide can be recovered to separate the fluorine compound or its salt between layers. Therefore, the burden to environment or the ecosystem by the fluorine compound can be reduced.

8 Claims, 2 Drawing Sheets

METHOD OF TREATING FLUORINE COMPOUNDS AND TREATED SUBSTANCE

FIELD OF THE INVENTION

Present invention relates to a treatment process reducing a burden to environment and ecosystem about a solution containing a molecular anion having a per-fluorocarbon chain as a main component. In addition, it is preferable that said treatment process recovers the above-mentioned anion to use effectively. Specifically, the present invention relates to a technology, which forms a layered double hydroxide to fix the molecular anion having the per-fluorocarbon chain as a main component in the solution, and recovers to reproduce these anions preferably.

BACKGROUND OF THE INVENTION

The anion surface-active agent having the per-fluorocarbon chain as a main component is used as an indispensable material of a production process in many fields, such as an emulsion polymerization process of PTFE (poly-tetra-fluoro-ethylene), and a production process of an electronic parts industry. Moreover, said anion surface-active agent is also widely used as a material, which are various paints, a coating agent, and a fire-extinguishing agent, etc. However, in these production processes, the above-mentioned anion surface-active agent has been used as a dilute solution, such as several % to 0.01% by weight, so that the efficient fixing and recovering said anion on an industrial scale has been difficult. Moreover, the problem of this fixing and recovering has not been considered in general because this solution is dilute. Furthermore, the fluorine compound, such as said anion surface-active agent, is a hard material to be processed by the activated sludge processing, which has been widely used as a wastewater processing. However, a harmony of chemical materials to environment or ecosystem is required strongly in recent years, and, also about this fluorine compound, it is started that the necessity of the technology about the closing system by fixing, recovering and reproducing is recognized strongly.

According to the fixing and recovering of this anion surface-active agent, the technology using the layered double hydroxide has been examined to be in practical use about a phosphate anion or an organic anion, as a scavenger or a removal agent of anions. However, about molecular anion having the per-fluorocarbon chain as a main component, such examinations have not been done previously. In addition, as a conventional technology, it is known that the process, in which an ammonium salt of fluoroalkane acid is extracted to recover by using an organic solvent, such as dichloro-methane or trichloro-methane, was proposed (Japanese Patent Raid Open No. Shou 61-215346), but this process uses an organic solvent containing chlorine, so that it is not enough for reducing the burden to environment.

In addition, the inventors have already reported the layered double hydroxide having anion between layers ($Zn_2Al(OH)_6C_7F_{15}CO_2$) for the purpose of a material synthesis (the 76th spring annual meeting of the Chemical Society of Japan), about a high concentration aqueous solution of per-fluoro-octanoic acid ammonium, i.e., about 8.6% by weight. However, this report was not for the purpose of fixing and recovering of the anion like this invention, about the solution having the wide concentration range including the dilute solution of 0.1% by weight. Therefore, the process about fixing of such fluorine compound has not been reported yet.

DISCLOSURE OF THE INVENTION

Present invention provides the treatment process, in which an organic fluorine compound having the per-fluorocarbon chain is fixed stably and easily, and its absorbing and fixing material. By this treatment process and material, the burden to environment and ecosystem can be reduced, and said fluorine compound can be used effectively as resources. Specifically, the present invention provides the treatment technology fixing to recover efficiently the anion having the per-fluorocarbon chain as the main component, such as carboxylic acid ion, sulfonic acid ion, etc., from the aqueous solution having the wide concentration range including the dilute aqueous solution of 0.1% by weight.

That is, this invention provides the process comprising the following constitution.

[1] A treatment process of a solution containing an organic compound having a fluorocarbon chain (hereinafter said to as the fluorine compound), the process comprising, adding divalent and trivalent metal salts to said solution, forming a layered double hydroxide having the fluorine compound between layers to absorb and fix the fluorine compound.

[2] A treatment process of a solution containing the fluorine compound, the process comprising, adding divalent and trivalent metal salts to said solution, precipitating a layered double hydroxide having the fluorine compound between layers, separating a solid part by a solid-liquid separation, dissolving said separated solid part in an acid, and separating a fluorine compound or its salt.

[3] The treatment process of the solution containing the fluorine compound according to above-mentioned process [1] or [2], the process further comprising, adjusting pH of the solution to more than 4, precipitating the layered double hydroxide having the fluorine compound between layers.

[4] The treatment process of the solution containing the fluorine compound according to above-mentioned process [1] or [2], the process further comprising, adding an alkali to the solution to adjust pH from 4 to 12, adding divalent and trivalent metal salts to said solution, and precipitating the layered double hydroxide having the fluorine compound between layers.

[5] The treatment process of the solution containing the fluorine compound according to any one of above-mentioned processes [1] to [4], wherein the divalent metal salt is a salt of magnesium, calcium, zinc, nickel, copper, manganese (divalent), or cobalt (divalent), and the trivalent metal salt is a salt of aluminum, iron, chromium, manganese (trivalent), cobalt (trivalent), potassium, lanthanum, or scandium.

[6] The treatment process of the solution containing the fluorine compound according to any one of above-mentioned processes [1] to [5], wherein the divalent and the trivalent metal salts are chlorides.

[7] The treatment process of the solution containing the fluorine compound according to any one of above-mentioned processes [1] to [6], wherein said fluorine compound is carboxylic acid or sulfonic acid having the fluorocarbon chain, in which the number of carbon is more than 5.

[8] The treatment process of the solution containing the fluorine compound according to any one of above-mentioned processes [1] to [7], wherein the layered double hydroxide having the fluorine compound between layers is shown in the following formula [1].

where Y is an anion having valence number m of the fluorine compound having the fluorocarbon chain, M(II) is a divalent metal ion, M(III) is a trivalent metal ion, X is 0.1 to 0.5, and n is 0 or positive integer.

[9] A treatment process for recovering the fluorine compound and its salts, the process comprising, precipitating the layered double hydroxide by the treatment process according to any one of above-mentioned processes [1] to [7], recovering the solid part by the solid-liquid separation, dissolving said recovered solid part in a mineral acid to recover the separated fluorine compound or its salts, or heating said mineral acid dissolving the recovered solid part, putting quietly to separate an oil layer, and taking out the oil layer to recover the fluorine compound and its salts.

[10] A treatment process for recovering a fluorine compound and its salts, the process comprising, precipitating the layered double hydroxide by the treatment process according to any one of above-mentioned processes [1] to [9], recovering the solid part by the solid-liquid separation, dispersing the recovered solid part to an organic solvent, and filtering an insoluble part from said solvent.

According to the above-mentioned processes of the present invention, the fluorine compound can be fixed stably to form the layered double hydroxide having the fluorine compound between layers, by adding divalent and trivalent metal salts to the solution containing the fluorine compound, such as the surface-active agent having the per-fluorocarbon chain. In addition, according to this treatment process, even when the concentration of the anion aqueous solution of the surface-active agent having the per-fluorocarbon chain is less than several % by weight, for example, very low concentration of about 0.01% by weight, this fluorine compound can be fixed with a very high rate of more than 90%. Moreover, as the adding metal salt, the safe salt to environment can be used, and the recovered layered double hydroxide is a solid, so that it can be processed advantageously in transportation or storage by drying.

Hereafter, this invention is explained concretely.

(A) Formation of the layered double hydroxide

Present invention is the treatment process, wherein the divalent and trivalent metal salts are added to the aqueous solution containing the anion of the organic fluorine compound having the fluorocarbon chain (the fluorine compound), such as carboxylic acid ion or sulfonic acid ion, etc., to form LDH containing said anion between the layers. By this process, the above-mentioned anion is fixed between the layers of LDH to separate this fluorine compound from the solution. Moreover, the present invention can be applied effectively to the solution containing the fluorine surface-active agent etc. as the fluorine compound having the fluorocarbon chain.

In the present invention, for example, the layered double hydroxide having the fluorine compound between the layers is the compound shown in the following formula [1]. In addition, it is available that this compound contains water or not.

where, Y is the anion having the valence number m of the fluorine compound having the fluorocarbon chain, M(II) is the divalent metal ion, M(III) is the trivalent metal ion, X is 0.1 to 0.4, and n is 0 or positive integer.

The layered double hydroxide of above formula [1] having the fluorine compound between layers is, for example, the compound that the anion A is replaced by the fluorine compound Y having the fluorocarbon chain, in the compound of the following formula [2].

where, A is the anion having the valence number m, M(II), M(III), X, and n are the same as the formula [1].

The divalent metal ion is each ion of magnesium, calcium, zinc, nickel, copper, manganese (divalent), or cobalt (divalent). Moreover, the trivalent metal ion is each ion of aluminum, iron, chromium, manganese (trivalent), cobalt (trivalent), gallium, lanthanum, or scandium. In these compounds, since the chloride is easy to receive and its reaction effect is also good, it is preferable to be used. Moreover, it is also available that these metal salts are the mixed compounds having two or more kinds of ion respectively. As the anion having the valence number m, carboxylic acid ion, sulfonic acid ion, chlorine ion and nitric acid ion etc. can be used.

The layered double hydroxide shown in the above-mentioned formula [1] can be formed by adjusting pH to more than 4, preferably 5 to 8, and adding the above-mentioned divalent and trivalent metal salts to the aqueous solution of the fluorine compound having the fluorocarbon chain. In addition, it is preferable that the addition of the metal salts is after or the same time at the adjustment of pH. Specifically, for example, the above-mentioned layered double hydroxide is precipitated by the way that the aqueous solution mixed with the above-mentioned divalent and trivalent metal salts is dropped gradually in the aqueous solution of the fluorine compound having the fluorocarbon chain, until the mole ratio becomes to the formula [1], and simultaneously alkali is dropped gradually to adjust pH of the solution to more than 4, preferably 5 to 8. Moreover, as alkali, conventional sodium hydroxide, and potassium hydroxide etc. can be used. In addition, when the divalent metal ion is calcium or magnesium, it is available that pH of the aqueous solution is in the range of 5 to 12. Regarding the addition of the divalent and trivalent metal salts, it is preferable that X value of mole ratio is 0.1 to 0.5 in the above-mentioned formula [1]. Usually, it takes about 3 hours for a natural precipitation of the separated substance at room temperature. In addition, it is preferable that the solution is stirred. The formed precipitate can be filtered to recover.

In the above-mentioned layered double hydroxide, the layered double hydroxide having the X value of about 0.33 in the formula [1], is not only having the large amount of reception capacity (the absorption capacity), but also making the stable compound between the absorbed anion and itself. Therefore, said layered double hydroxide is the most preferable for fixing and recovering the absorbed anion. Moreover, both of the divalent metal ion of zinc or magnesium and the trivalent metal ion of aluminum or iron, which can form the layered double hydroxide, are safe and harmless to environment. In addition, chlorine ion and Na ion used in the forming process of this layered double hydroxide are also safe and harmless to environment. Furthermore, by controlling pH of the aqueous solution to near neutral, the influence to environment by the wastewater can also be removed substantially.

In addition, as mentioned above, when the precipitate of the layered double hydroxide having fluorine compound between layers is formed, before adjusting pH of the solution and adding the metal salts, it is preferable that the inert gas is bubbled beforehand in the solution containing the fluorine compound and the polymer containing fluorine to drive out the carbonic acid contained in the solution. If the carbonic acid is remained in the solution, the metal salts and the alkali will react with carbonic acid, so that it is not preferable.

According to the above-mentioned process for forming the layered double hydroxide, the objective anion of the fluorine compound having the fluorocarbon chain can be fixed with high efficiency of more than 60%, preferably more than 90%. In addition, the formed precipitate containing the layered double hydroxide can be separated by the conventional method of the solid-liquid separation. As the concrete separation equipment or method, for example, the filtering, a decantation, a centrifugation, a thickener, a filter press, a precoat, and a body field, etc. can be used. In addition, it is not limited to these.

(B) Recovering the Fluorine Compound.

The process for separating the fluorine compound from the recovered layered double hydroxide shown with the formula [1] is the followings. The precipitate of this layered double hydroxide is dissolved in the mineral acid having pH of less than 1. At this time, since the fluorine compound is remained in the strong acid without dissolving, this remained fluorine compound is recovered by the solid-liquid separation. On the other hand, when the liquid temperature of this solution is more than the fusion temperature of the fluorine compound or its salt, since this fluorine compound is liquefied, the fluorine compound or its salt can be recovered by putting quietly to take out the separated oil layer.

Specifically, for example, the precipitated layered double hydroxide is recovered by the solid-liquid separation, and the recovered substance is dissolved in sulfuric acid etc. having pH of less than 1. At this time, the divalent and trivalent metal components in the layered double hydroxide are dissolved. Moreover, when the liquid temperature is higher than the fusion temperature of the fluorine compound or its salt, the fluorine compound or its salt is liquefied. Therefore, as putting quietly this solution at more than the above-mentioned fusion temperature, the water layer containing the divalent and trivalent metal ions and the oil layer containing the fluorine compound or its salt can be separated to take out this oil layer. The fluorine compound, such as carboxylic acid, can be recovered with high purity and high yield by refining this oil layer by distillation etc.

In addition, when the precipitated layered double hydroxide is mixed with sulfuric acid etc. having pH of less than 1, the temperature of the solution is raised by heating of dilution. From this reason, when the liquid temperature becomes more than the fusion temperature of the fluorine compound or its salt, it is preferable that this solution is put quietly to keep this temperature. Moreover, when the liquid temperature is low, it is preferable that said liquid is heated, so that it may become more than the fusion temperature. According to such separation of liquid and liquid, the fluorine compound can be separated more advantageously than the solid-liquid separation.

As another process, it is also available that the fluorine compound is separated as the solid part, by the solid-liquid separation of the solution, where the precipitate was dissolved in the strong acid at the liquid temperature of less than the above-mentioned fusion temperature.

The recovery process using an ion exchange can be used other than the above-mentioned process, which dissolves the precipitate in the strong acid. That is, the precipitate containing the layered double hydroxide etc., which is separated by the solid-liquid separation, is dispersed in the aqueous solution of carbonate, such as sodium carbonate. At this time, the divalent and trivalent metal ions, which has been fixed in the layered double hydroxide, are ion-exchanged by the carbonate ion, and to be eluted in the liquid. Then, the solid part is recovered by the solid-liquid separation of said solution, and dissolved in an alcohol. The insoluble part in the alcohol is filtered, so that the fluorine compound or its salt can be recovered.

(C) Application

According to the treatment process of the present invention, wherein the fluorine compound can be absorbed and fixed by forming the layered double hydroxide having the fluorine compound between layers, the process can be developed into the various methods, such as the ion exchanging method, in which the fluorine compound is absorbed and fixed on the preformed layered double hydroxide having good ion exchange ability shown in the above-mentioned formula [2], and a re-hydrating method, in which the solid part formed by the above-mentioned absorbed and fixed process, i.e. the absorbing and fixing material, is baked to reproduce the absorption ability for reusing, etc.

As mentioned above, in the treatment process of the present invention, although the compound between LDH layers is formed as the fixing compound, in this structure, the positive charged metal hydroxide layer and the anion layer compensating the positive charge, are laminated between said metal hydroxide layers. The schematic structure of this layered double hydroxide is shown in FIG. 3. It has been known generally that the characteristics of this structure have a function as the ion exchange between anions and an anion scavenger. However, by using this structure, the present invention provides the preferable state for the solid layer formation by the self-coagulation-interaction (hydrophobic bond) of the per-fluorocarbon chain having a remarkable hydrophobic property, with a micro level. By providing the preferable state, the present invention fixes the objective anion stably between layers, by using the multiplication-effect between the self-coagulation interaction of the per-fluorocarbon chain and the electrostatic interaction between layers of the layered double hydroxide. Such ideas of the present invention have not been known conventionally.

Hereinafter, the treatment process of the present invention is explained concretely with the examples.

EXAMPLE 1

1000 ml of the aqueous solution of per-fluoro-octanoic acid ammonium ($C_7F_{15}COONH_4$) of 0.1% by weight, wherein the anion for the purpose of absorption was 2.32 mmol, was put into the glass beaker, and the mixed solution of zinc chloride and aluminum chloride, wherein $Zn^{2+}$ ion was 4.64 mmol and $Al^{3+}$ ion was 2.32 mmol, was dropped gradually in this solution. Simultaneously, 2 mol/l of the aqueous solution of sodium hydroxide was also dropped to adjust pH to 7. This process was done for 3 hours. Immediately after the dropping of the mixed aqueous solution, the aqueous solution became cloudy to form the white precipitate with progress of time, and this liquid cloudiness was finished to complete the precipitate forming after 3 hours. The precipitate was filtered to recover, and dried at 70° C. until the constant weight to be 1.50 g.

Figure 1:
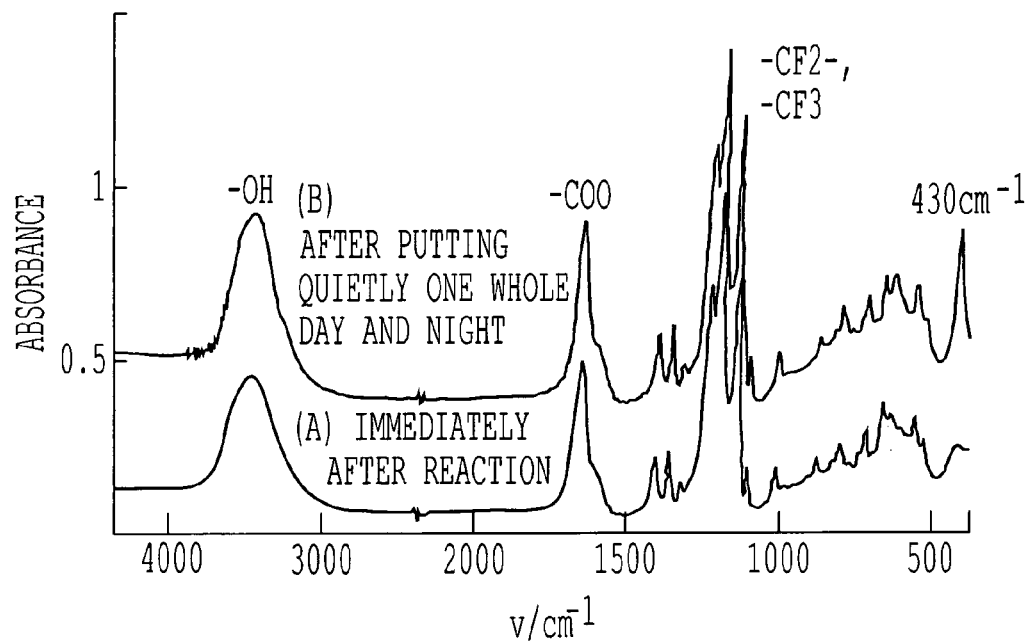
FIG. 1 shows the IR spectrum ratio of the precipitate (a) at ending time of dropping, and (b) after putting quietly for one whole day and night, in Example 1.
Figure 2:
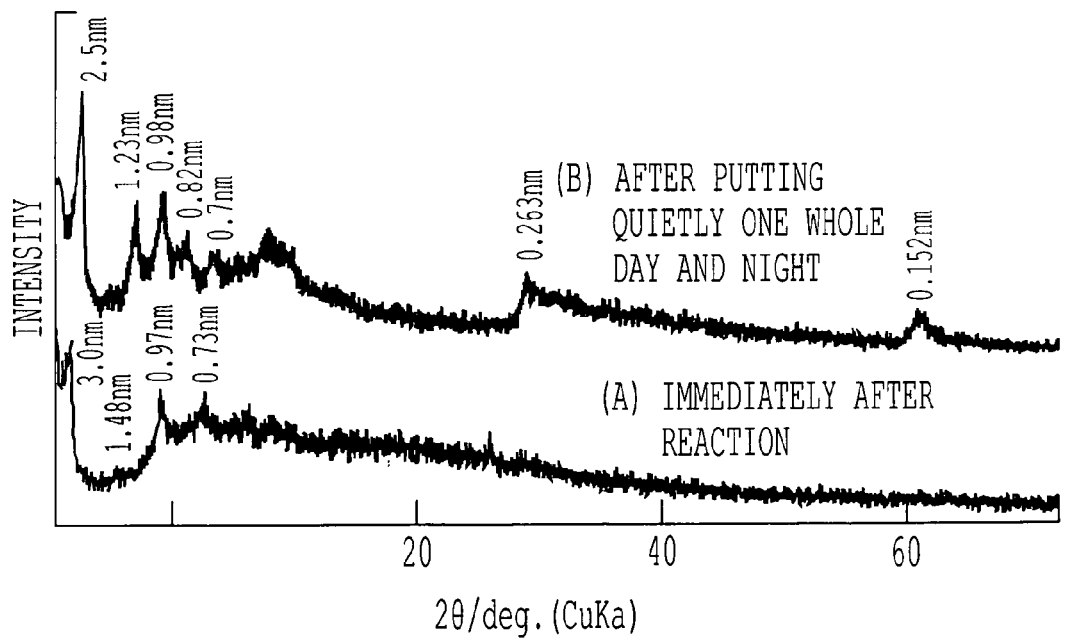
FIG. 2 shows XRD patterns of the precipitate (a) at ending time of dropping, and (b) after putting quietly for one whole day and night, in Example 1.
Figure 3:
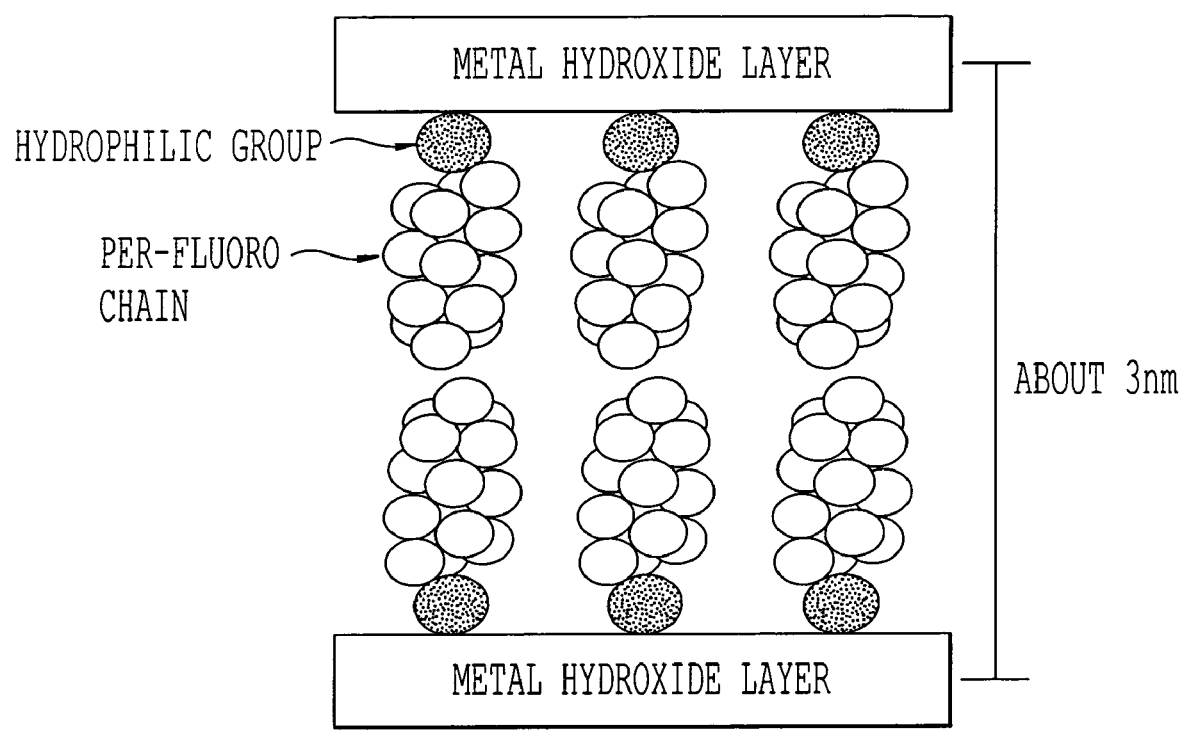
FIG. 3 is a schematic structure showing the layered double hydroxide (recovered precipitate) of the present invention.

1 mg of this powder was taken, and the infrared absorption spectrum was measured by the KBr tablet method. The result of the spectra is shown in FIG. 1. The spectra immediately after reaction is shown in FIG. 1(a), and the spectra after putting quietly one whole day and night is shown in FIG. 1(b). In these spectra, the strong absorption peculiar to the per-fluorocarbon chain, and the absorption of a hydroxyl group peculiar to LDH layer, were observed, so that it was confirmed that these spectra were the layered double hydroxide ($Zn_2Al(OH)_6C7F_{15}CO_2$). By this chemical formula and weight, the amount of anions in the solid layer was calculated to be 2.23 mmol, and this amount was equivalent to 96.1% by weight of anions first dissolved in the aqueous solution.

Moreover, the powder at the ending time of dropping was taken out to put on the glass plate to make a film for measuring by XRD. From the result of XRD, the diffraction belonging to the basal plane space of about 3.0 nm was shown, and the high-dimension reflections belonging to this diffraction were also shown. Considering the length of the absorbed anion, i.e. 1.25 nm, and the thickness of LDH, i.e. 0.48 nm, it was supposed that the layered compound involving two molecules layer between layers, was formed.

Moreover, the dried powder separated by putting quietly one whole day and night after reaction, was measured by XRD. From the result of XRD, the basal plane space was reduced to about 2.50 mm, and, at the positions of 0.263 nm and 0.152, the reflections of (100) plane and (110) plane corresponding to hexagonal lattice in the LDH layer, were observed. These reflections indicated that the lattice constant [a] was 0.304 nm, and the hydroxide layer, in which the ions of aluminum and zinc were mixed, was formed to grow up in this structure. Moreover, in the sample (b), the basal plane space was reduced compared with the above-mentioned sample (a), and the super lattice line corresponding to the period of the twice length of the sample (a), was appeared. From this result, it was supposed that the regulation of the anion arrangement between layers was advanced to transfer to the more closed structure. In addition, when IR spectra of these both samples were compared, there were no fundamental differences excepting that the absorption band of the lattice vibration of the metal hydroxide layer near 430 $cm^{-1}$ was radicalized with improvement of the crystal regularity. Therefore, it was considered that this change was done by the regulation of molecule arrangement in the structure, and the incorporation of the objective anion to the solid phase was finished mostly at the time of the ending of dropping.

On the other hand, the solution after filtering the precipitate (the supernatant liquor), was measured by the calorimetric method using methylene blue. The calibration curve was made by following ways. Five kinds of standard solution, in which 1 to 5 ppm by weight of ammonium salt of the above-mentioned negative ions was contained, were prepared, and 30 ml of said standard solution was taken respectively to the separatory funnels to be added 10 ml of chloroform and 10 ml of methylene-blue solution. After shaking well, these solution were put quietly for 10 minutes and calibration curve was made by measuring the each absorbance of these solutions using a visible/ultraviolet spectrometer. The measuring wavelength was fixed at 635 nm. The absorbance value was in the range of 0 to 1 in this concentration range, and the calibration curve showed good linearity. The same process was done to the supernatant liquor. At this time, said supernatant liquor was diluted to become in the range of 0 to 1 of the absorbance, if necessary. As a result, the concentration of the above-mentioned anionic surface-active agent (per-fluoro-octanoic acid ammonium) was 10 ppm. This result means that 96% of the above-mentioned anions were fixed to the initial concentration (0.1% by weight), and was corresponded with the previous result by the solid weight. These results were shown in No. 1 of Table 1.

EXAMPLE 2

Regarding the aqueous solution, where the concentration was different from Example 1, the per-fluoro-octanoic acid ion was absorbed and fixed by the same process as Example 1. 100 ml of the aqueous solution containing the objective anion ammonium salt of 1.0% by weight (the aqueous solution A), and 1.01 of the aqueous solution containing said anion ammonium salt of 0.01% by weight (the aqueous solution B), were prepared respectively. In addition, 35 ml of the same mixed solution of the zinc chloride and aluminum chloride as Example 1, was dropped gradually in the aqueous solution A, and 3.5 ml of said mixed solution was dropped gradually in the aqueous solution B. This process was done for 3 hours. At this time, pH of the aqueous solutions of A and B were adjusted to 7 by using the sodium hydroxide of 2 mol/l. This dropping was done at room temperature, and the temperature was not controlled. After dropping, said aqueous solution was put quietly overnight to filter the supernatant liquor, and the weight of the dried solid part, the anion concentration, and the fixing ratio of anions, were measured like Example 1. These results were shown in No.2 of Table 1.

EXAMPLE 3

The precipitate was formed like Example 1 excepting that the mixed aqueous solution of zinc chloride and aluminum chloride was added to the aqueous solution of per-fluoro-octanoic acid ammonium to adjust pH to 5. Then, 1.50 g of the precipitate was recovered by filtering and drying. After forming the precipitate, the solution was put quietly overnight to filter the supernatant liquor. Then, the weight of the solid part after drying, the anion concentration, and the fixing ratio of anions, were measured like Example 1. These results were shown in No. 3 of Table 1.

EXAMPLE 4

The precipitate was formed like Example 1 excepting that about 35 ml of the mixed aqueous solution of magnesium chloride and aluminum chloride, wherein $Mg^{2+}$ ion was 4.64 mmol, and $Al^{3+}$ ion was 2.32 mmol, was used as the mixed solution, and pH of the solution after dropping was adjusted to 10. Then, 1.10 g of the precipitate was recovered by filtering and drying. When the recovered precipitate was analyzed by XRD and the infrared absorption spectrum, it was confirmed that said precipitate was the layered double-hydroxide [$Mg_2Al(OH)_6C_7F_{15}CO_2$]. After forming the precipitate, the solution was put quietly overnight to filter the supernatant liquor. In addition, the weight of the solid part after drying, the anion concentration, and the fixing ratio of anions, were measured like Example 1. These results were shown in No.4 of Table 1.

EXAMPLE 5

The precipitate was formed like Example 1 excepting that about 35 ml of the mixed aqueous solution of calcium chloride and aluminum chloride, wherein $Ca^{2+}$ ion was 4.64 mmol, and $Al^{3+}$ ion was 2.32 mmol, was used as the mixed solution, and pH of the solution after dropping was adjusted to 10. Then, 0.85 g of the precipitate was recovered by filtering and drying. When the recovered precipitate was analyzed by XRD, and the infrared absorption spectrum, it was confirmed that said precipitate was the layered double hydroxide $[Ca_2Al(OH)_6C_7F_{15}CO_2]$. After forming the precipitate, the solution was put quietly overnight to filter the supernatant liquor. In addition, the weight of the solid part after drying, the anion concentration, and the fixing ratio of anions, were measured like example 1. These results were shown in No.5 of Table 1.

EXAMPLE 6

The precipitate was formed like Example 1 excepting that the solution of per-fluoro-octyl sulfonic-acid ammonium $(C_8F_{17}SO_3NH_4)$ of 0.1% by weight, wherein the anion for the purpose of absorption was 2.32 mmol, was used as the solution. Then, 1.70 g of the precipitate was recovered by filtering and drying. When the recovered precipitate was analyzed by XRD and the infrared absorption spectrum, it was confirmed that said precipitate was the layered double hydroxide $[Zn_2Al(OH)_6C_8F_{17}SO_3]$. After forming the precipitate, the solution was put quietly overnight to filter the supernatant liquor. In addition, the weight of the solid part after drying, the anion concentration, and the fixing ratio of anions, were measured like Example 1. These results were shown in No.6 of Table 1.

EXAMPLE 7

The precipitate was formed like Example 1 excepting that the solution of per-fluoro-octyl sulfonic-acid lithium $(C_8F_{17}SO_3Li)$ of 0.1% by weight, wherein the anion for the purpose of absorption was 2.32 mmol, was used as the solution. Then, 1.45 g of the precipitate was recovered by filtering and drying. When the recovered precipitate was analyzed by XRD and the infrared absorption spectrum, it was confirmed that said precipitate was the layered double hydroxide $[Zn_2Al(OH)_6C_8F_{17}SO_3]$. After forming the precipitate, the solution was put quietly overnight to filter the supernatant liquor. In addition, the weight of the solid part after drying, the anion concentration, and the fixing ratio of anions, were measured like Example 1. These results were shown in No.7 of Table 1.

EXAMPLE 8

3 kg of dilute sulfuric acid having the concentration of 10 wt %, was put into the glass beaker, where the capacity was 3 L, to add 300 g of the precipitate (the layered double hydroxide) recovered in Example 1. In addition, said solution was stirred to dissolve for 3 hours at room temperature. After that, said dissolved solution was put quietly at 70° C., and the aqueous solution layer containing Zn ion and Al ion, and the oil layer comprising per-fluoro-octanoic acid, were separated. When this oil layer was taken out to distill, 172 g of the main fraction of per-fluoro-octanoic acid, wherein the temperature at the top of the column was from 170 to 192° C., was recovered. The purity of this recovered substance was 99%, and the containing amount of Zn and Al was less than 1 ppm.

EXAMPLE 9

400 g of the sodium carbonate aqueous solution having the concentration of 10 wt %, was put into the glass beaker, where the capacity was 500 ml, to add 20 g of the precipitate (the layered double hydroxide) recovered in Example 1. In addition, said solution was stirred to dissolve for 24 hours at room temperature. Then, 22.2 g of crystal was recovered by filtering and drying. This crystal was added to 300 ml of methanol to be stirred for 1 hour at room temperature to disperse. The insoluble solid part was filtered to take out methanol by the distillation from the filtrate. Then, 12.2 g of white crystal was recovered. When the insoluble solid part was analyzed by the IR spectrum, it was confirmed that the insoluble solid part comprised the substance that the anion parts of the layered double hydroxide were replaced by the carbonate ions. Furthermore, it was also confirmed that the white crystal recovered by concentrating the filtrate has the per-fluoro-octanoic acid sodium as the main component.

EXAMPLE 10

The precipitate was formed like Example 1 excepting that the aqueous solution of per-fluoro-decanoic acid ammonium $(C_9F_{19}COONH_4)$ of 0.05% by weight, wherein the anion for the purpose of absorption was 1.16 mmol, and the mixed aqueous solution of zinc chloride and aluminium chloride, wherein $Zn^{2+}$ ion was 2.32 mmol, and $Al^{3+}$ ion was 1.16 mmol, in the mixed solution, were used. Then, 0.84 g of precipitate was recovered by filtering and drying. When this recovered precipitate was analyzed by XRD and the infrared absorption spectrum, it was confirmed that said precipitate was the compound containing per-fluoro-decanoic acid ammonium $(C_9F_{19}COONH_4)$. After forming the precipitate, the solution was put quietly overnight to filter the supernatant liquor. The weight of the solid part after drying, the anion concentration, and the fixing ratio of anions, were measured like Example 1. These results were shown in No. 10 of Table 1.

INDUSTRIAL APPLICABILITY

According to the process of the present invention, it is possible that the fluorine compound, such as the surface-active agent having the per-fluorocarbon chain, can be absorbed and fixed stably between the layers of the layered double hydroxide. The formation of the layered double hydroxide and the absorption of the fluorine compound are progressed simultaneously in the solution, and this layered double hydroxide is formed easily by adding the divalent and trivalent metal salts, so that the above-mentioned fluorine compound can be absorbed and fixed easily. Moreover, in the suitable embodiment, when the concentration of the anion aqueous solution of the surface-active agent having the per-fluorocarbon chain is less than several % by weight, for example, very low concentration of about 0.01% by weight, this fluorine compound can be fixed at a very high rate of more than 90%. In addition, as the adding metal salts, the safe ones to environment can be used. Moreover, since the layered double hydroxide can be recovered as a solid, it is advantageously in transportation or storage. Furthermore, according to the treatment process of the present invention, the fluorine compound fixed at the layered double hydroxide can be recovered efficiently by the separation to be reused. Therefore, the burden to environment and ecosystem with the fluorine compound can be reduced, and the fluorine compound can be reused as the resources.

TABLE 1

| No. | Fluorine Compound Solution Kinds | Concentration, Amount | Amount of Anion | Additional Metal Salt Divalent | Additional Metal Salt Trivalent | Solution pH | Precipitate Amount | Precipitate Anion Concentration | Anion Fixing Ratio |
|---|---|---|---|---|---|---|---|---|---|
| 1 | Per-fluoro-octanoic acid ammonium ($C_7F_{15}COONH_4$) | Aqueous solution of 0.1%, 1000 ml | 2.32 mmol | Zn 4.64 mmol | Al 2.32 mmol | 7 | 1.50 g | 2.23 mmol | 96.1% |
| 2 | Per-fluoro-octanoic acid ammonium ($C_7F_{15}COONH_4$) | Aqueous solution of 0.1%, 1000 ml | 2.32 mmol | Zn: 4.64 mmol | Al: 2.32 mmol | 7 | 1.50 g | 2.3 mmol | 99.1% |
|   |   | Aqueous solution of 0.1%, 1000 ml | 0.232 mmol | Zn: 0.464 mmol | Al: 0.232 mmol |   | 0.15 g | 0.21 mmol | 91.0% |
| 3 | Per-fluoro-octanoic acid ammonium ($C_7F_{15}COONH_4$) | Aqueous solution of 0.1%, 1000 ml | 2.32 mmol | Zn 4.64 mmol | Al 2.32 mmol | 5 | 1.50 g | 2.27 mmol | 98% |
| 4 | Per-fluoro-octanoic acid ammonium ($C_7F_{15}COONH_4$) | Aqueous solution of 0.1%, 1000 ml | 2.32 mmol | Mg 4.64 mmol | Al 2.32 mmol | 10 | 1.10 g | 1.4 mmol | 80% |
| 5 | Per-fluoro-octanoic acid ammonium ($C_7F_{15}COONH_4$) | Aqueous solution of 0.1%, 1000 ml | 2.32 mmol | Ca 4.64 Mmol | Al 2.32 mmol | 10 | 0.85 g | 2.3 mmol | 60% |
| 6 | Per-fluoro-octyl-sulfonic acid Ammonium ($C_8F_{17}SO_3NH_4$) | Aqueous solution of 0.1%, 1200 ml | 2.32 mmol | Zn 4.64 mmol | Al 2.32 mmol | 7 | 1.70 g | 2.23 mmol | 99% |
| 7 | Per-fluoro-octyl-sulfonic acid lithium ($C_8F_{17}SO_3Li$) | Aqueous solution of 0.1%, 117 ml | 2.32 mmol | Zn 4.64 mmol | Al 2.32 mmol | 7 | 1.65 g | 2.2 mmol | 95% |
| 10 | Per-fluoro-decanoic acid Ammonium ($C_9F_{19}COONH_4$) | Aqueous solution of 0.005%, 1000 ml | 1.161 mmol | Zn 2.32 mmol | Al 2.32 mmol | 7 | 0.84 g | 1.09 mmol | 94% |

What is claimed is:

1. A layered double hydroxide of formula (I), $$M(II)_{1-x}M(III)_x(OH)_2Y_{x/m} \cdot nH_2O \quad (I)$$

wherein, Y is an anion of an organic fluorine compound having a fluorocarbon chain, and a valence number of m,
M(II) is a divalent metal ion,
M(III) is a trivalent metal ion,
X is 0.1 to 0.5, and
n is a positive integer,
wherein the layered double hydroxide is a solid obtained by
adding one or more divalent and trivalent metal salts to a solution comprising the organic fluorine compound having a fluorocarbon chain to precipitate the layered double hydroxide wherein the layered double hydroxide has the fluorine compound present between layers, and
separating the precipitate by solid-liquid separation.

2. The hydroxide according to claim 1, wherein, M(II) is a divalent ion of Mg or Ca, and M(III) is a trivalent ion of Al or Fe.

3. The hydroxide according to claim 1, wherein Y is an anion of a carboxylic acid or sulfonic acid having a fluorocarbon chain having more than 5 carbon atoms.

4. The hydroxide according to claim 1, wherein the hydroxide is a resource to reuse the fluorine compound.

5. The hydroxide according to claim 1, wherein X=⅓, m=1, and the formula of the hydroxide is:

$$M(II)_2M(III)(OH)_6Y \cdot nH_2O.$$

6. The hydroxide according to claim 5,
wherein, M(II) is a divalent ion of Mg or Ca, and M(III) is a trivalent ion of Al or Fe.

7. The hydroxide according to claim 5, wherein Y is an anion of a carboxylic acid or a sulfonic acid having a fluorocarbon chain having more than 5 carbon atoms.

8. The hydroxide according to claim 5,
wherein the hydroxide is a resource to reuse the fluorine compound.

* * * * *